US009456756B2

(12) United States Patent
Warnking et al.

(10) Patent No.: US 9,456,756 B2
(45) Date of Patent: Oct. 4, 2016

(54) SYSTEM FOR DETECTION OF BLOOD PRESSURE USING A PRESSURE SENSING GUIDE WIRE

(75) Inventors: Reinhard J. Warnking, Palm Beach Gardens, FL (US); Matthew J. Pollman, San Francisco, CA (US)

(73) Assignee: Guided Interventions, LLC, Elyria, OH (US)

( * ) Notice: Subject to any disclaimer, the term of this patent is extended or adjusted under 35 U.S.C. 154(b) by 521 days.

(21) Appl. No.: 13/978,822

(22) PCT Filed: Jan. 30, 2012

(86) PCT No.: PCT/US2012/023130
§ 371 (c)(1),
(2), (4) Date: Jul. 25, 2013

(87) PCT Pub. No.: WO2012/109039
PCT Pub. Date: Aug. 16, 2012

(65) Prior Publication Data
US 2013/0296722 A1   Nov. 7, 2013

Related U.S. Application Data

(60) Provisional application No. 61/437,654, filed on Jan. 30, 2011.

(51) Int. Cl.
*A61B 5/0215* (2006.01)
*A61B 5/00* (2006.01)
*A61M 25/09* (2006.01)

(52) U.S. Cl.
CPC ......... *A61B 5/02152* (2013.01); *A61B 5/0015* (2013.01); *A61B 5/0215* (2013.01); *A61B 5/6851* (2013.01); *A61M 25/09* (2013.01); *A61M 2025/09175* (2013.01)

(58) Field of Classification Search
CPC ............. A61B 5/0015; A61B 5/6851; A61M 2025/09175
See application file for complete search history.

(56) References Cited

U.S. PATENT DOCUMENTS

| 3,281,748 A | * | 10/1966 | La Rosa | ................ H01F 21/04 336/137 |
| 6,217,518 B1 | * | 4/2001 | Holdaway | ............ A61B 5/6848 600/439 |
| 6,957,098 B1 | * | 10/2005 | Hyde | ..................... A61B 5/055 600/424 |

(Continued)

FOREIGN PATENT DOCUMENTS

| JP | 2000-507142 A | 6/2000 |
| JP | 2003-265617 A | 9/2003 |

(Continued)

OTHER PUBLICATIONS

U.S. Appl. No. 06/053,873, filed Apr. 25, 2000, Govari et al.

(Continued)

*Primary Examiner* — Jacqueline Cheng
*Assistant Examiner* — Angeline Premraj
(74) *Attorney, Agent, or Firm* — R. Neil Sudol; Henry D. Coleman (57) ABSTRACT

A guide wire has a distal end incorporating a coil and a capacitive element that form a resonance circuit with a resonance frequency that is responsive to the pressure of blood external to the guide wire. The resonance frequency can be detected wirelessly, or through two contacts at the proximal wire end, or through one brush contact located inside an insertion sheath and a ground electrode. Wireless detection can be implemented via a second resonance circuit, and electronics for determining the frequency when the first and second circuits are in resonance with each other.

16 Claims, 10 Drawing Sheets

(56) References Cited

U.S. PATENT DOCUMENTS

| | | |
|---|---|---|
| 7,418,289 B2 | 8/2008 | Hyde et al. |
| 2002/0013527 A1 | 1/2002 | Hoek et al. |
| 2002/0151816 A1* | 10/2002 | Rich .................. A61B 5/0031 600/547 |
| 2003/0028095 A1* | 2/2003 | Tulley ............ G01R 33/34053 600/422 |
| 2003/0139677 A1 | 7/2003 | Fonseca |
| 2004/0260346 A1* | 12/2004 | Overall ............ A61B 5/02444 607/4 |
| 2005/0159659 A1* | 7/2005 | Sawan .................. A61B 5/037 600/380 |
| 2006/0117859 A1* | 6/2006 | Liu .................... A61B 5/02152 73/753 |
| 2007/0293904 A1 | 12/2007 | Gelbart |
| 2008/0132806 A1* | 6/2008 | Smith .................... A61B 5/036 600/585 |
| 2010/0022896 A1* | 1/2010 | Yadav .................. A61B 5/0031 600/488 |

FOREIGN PATENT DOCUMENTS

| | | |
|---|---|---|
| JP | 2009-226012 A | 10/2009 |
| WO | WO 98/29030 A1 | 7/1998 |

OTHER PUBLICATIONS

U.S. Appl. No. 06/113,553, filed Sep. 5, 2000, Chubbuck, John.

* cited by examiner

SYSTEM FOR DETECTION OF BLOOD PRESSURE USING A PRESSURE SENSING GUIDE WIRE

FIELD OF THE INVENTION

The present invention is related to a system (apparatus and method) for detection of blood pressure in a blood vessel, and in particular to a system having a guide wire with a sensor for sensing pressure of the blood.

BACKGROUND OF THE INVENTION

Interventional cardiologists rely on guide wires to reach the treatment site inside a blood vessel, such as the coronary arteries. Instead of utilizing the guide wire as a strictly mechanical or guiding tool, pressure and flow wires are being promoted as a dual function guide wire, providing mechanical guidance and hemodynamic information at the same time. Based on the results of the FAME study, FFR (Fractional Flow Reserve) measurements are becoming popular and in several countries the costs of such measurements are reimbursed. Currently there are 2 types of pressure wires commercially available: Radi (acquired by STJ) and Volcano. Both guide wires use an IC pressure sensor (strain gage type) connected through a push on handle with 3 electrical contacts at the proximal wire end. In case of the Radi guide wire, the connector handle wirelessly transmits pressure values to a display system. While this FFR device is an improvement over a cable connection, it is still very cumbersome, since for every catheter insertion the connector handle must be disconnected from the proximal wire end before the catheter can be advanced over the wire.

SUMMARY OF THE INVENTION

The present invention recognizes that a truly wireless transmission, or transmission through a sheath contact, of pressure data from a resonance circuit at a distal end of a cardiovascular guide wire to a pressure monitoring system greatly enhances clinical utility because catheters can be inserted over the wire without having to disconnect a handle. In such a system the wire really functions as a mechanical guide for catheter insertions and as a hemodynamic measurement tool. A two-contact version while requiring a handle, still has an advantage over current wires in that the guide wire characteristics are not compromised through electrical wires running inside the guide wire since the inner core wire and outer hypotube, of which a typical wire consists, will be utilized as electrical conductors.

The present invention contemplates a system for detection of blood pressure in a blood vessel, where the system comprises a guide wire, a coil provided at a distal end of the guide wire, and a capacitor provided at a distal end of the guide wire. The coil and the capacitor are coupled to each other to form a resonance circuit, and at least one of the coil and the capacitor is responsive to changes in pressure of fluid external to the guide wire such that the resonance circuit has a resonance frequency that varies in accordance with changes in pressure of the external fluid. Thus, the resonance circuit has an LC parameter (inductance or capacitance) that varies in accordance with pressure of a fluid surrounding a distal end portion of the guide wire.

In accordance with one embodiment of the present invention, a blood-pressure detection system includes a guide wire having a distal portion with a coil and pressure sensitive capacitive element providing a first resonance circuit which varies in its resonance frequency depending on the pressure of blood external to the guide wire when in a blood vessel of a patient's body. The floppy tip that a typical guide wire has at the distal end may serve as the coil or inductor of the resonance circuit. Accordingly no additional electrical components are required except for a very small capacitive sensor to be so integrated into the guide wire that the wire maintains its original mechanical handling characteristics.

In another embodiment of the present invention, the resonance frequency, which is indicative of blood pressure, is detected through two electrical contacts at the proximal wire end. In another embodiment the resonance frequency is read via a single brush contact inside a sheath through which the guide wire is inserted and a ground electrode on the patient. In yet another embodiment a detector includes a second resonance circuit which is operatively connectable to the first resonance circuit (on the guide wire). The detector incorporates electronics for determining the frequency when the first and second circuits are in resonance with one another. This frequency of resonance corresponds to blood pressure about the distal end of the guide wire.

The pressure sensitive capacitive element of the first resonance circuit represents a variable capacitive element with at least one pressure sensitive element, e.g., a membrane, which varies the capacitance responsive to the amount of pressure applied external of the guide wire onto the membrane. These pressure sensitive capacitors are well known and described in Journal of Micromechanics and Micro-engineering, Volume 17, July 2007: A fast telemetric pressure and temperature sensor system for medical applications; R Schlierf, U Horst, M Ruhl, T Schmitz-Rode, W Mokwa and U Schnakenberg; Sensors and Actuators A: Physical, Volume 73, issues 1-2, March 1999: Low power integrated pressure sensor system for medical applications; C Hierold, B Clasbrummel, D Behrend, T Scheiter, M Steger, K Oppermann, H Kapels, E Landgraf, D Wenzel and D Etzrodt; 2010 IEEE International Solid-State Circuits Conference: Mixed-Signal Integrated Circuits for Self-Contained Sub-Cubic Millimeter Biomedical Implants; Eric Y Chow, Sudipto Chakraborty, William J Chappell, Pedro P Irazoqui).

The first resonance circuit may be integrated at the distal end of a typical guide wire, such as a coronary ($14/1000$ of an inch) guide wire utilizing the floppy tip of the guide wire as an inductor. The resonance frequency is exemplarily detected wirelessly through an external second resonance circuit which supplies electro-magnetic energy to the first resonance circuit inside the guide wire. The transmitted energy to first resonance circuit from the second resonance circuit varies depending on resonance frequency fluctuations caused by a capacitive element of the pressure sensor which is coupled to the coil. In an alternative embodiment, the pressure sensitive element of the guide wire's resonance circuit is the inductor or coil. As discussed hereinbelow, pressure monitoring may be implemented by varying the number of active coil windings, the length of the inductor, or the degree of insertion of a ferromagnetic core in dependence on the external blood pressure. In other embodiments the resonance frequency is detected through 2 electrical contacts at the wire end and a handle, or through an electrical contact within the sheath which holds the wire and a ground connection. A method measuring blood pressure comprises, in accordance with the present invention, inserting a distal end portion of an elongate wire into a cardiovascular system of a patient, where the distal end portion is provided with an LC resonance circuit. The method further comprises detecting a resonance frequency of the LC resonance circuit while the circuit is inside the vascular system of the patient and determining a blood pressure value from the detected resonance frequency.

Pursuant to additional features of the invention, where the LC resonance circuit includes a circuit element with an LC parameter varying in accordance with pressure of a fluid surrounding the distal end portion of the wire, the method further comprises monitoring the resonance circuit for a change in the resonance frequency owing to a variation in the LC parameter induced by a blood pressure change and; determining a second blood pressure value from the changed resonance frequency. Accordingly, blood pressure can be monitored continuously.

Where the LC parameter is inductance, the method further comprises varying the inductance in accordance with blood pressure by changing a physical parameter taken from the group consisting of coil length, number of active windings in an inductor, and extent of insertion of a movable ferromagnetic core member into an inductor or coil.

BRIEF DESCRIPTION OF THE DRAWINGS

The foregoing objects, features and advantages of the invention will become more apparent from a reading of the following description in connection with the accompanying drawings, in which:

FIGS. 4A and 4B are two photographs illustrating the operation of two resonance circuits which may represent a sensor circuit and a detector circuit of the present invention, where FIG. 4A shows the sensor circuit and the detector circuit in resonance and accordingly a high current on an oscilloscope, and FIG. 4B shows the sensor circuit detuned with an additional capacitor which reduces the current into the detector circuit and therewith the current on the oscilloscope.

DETAILED DESCRIPTION

Figure 1:
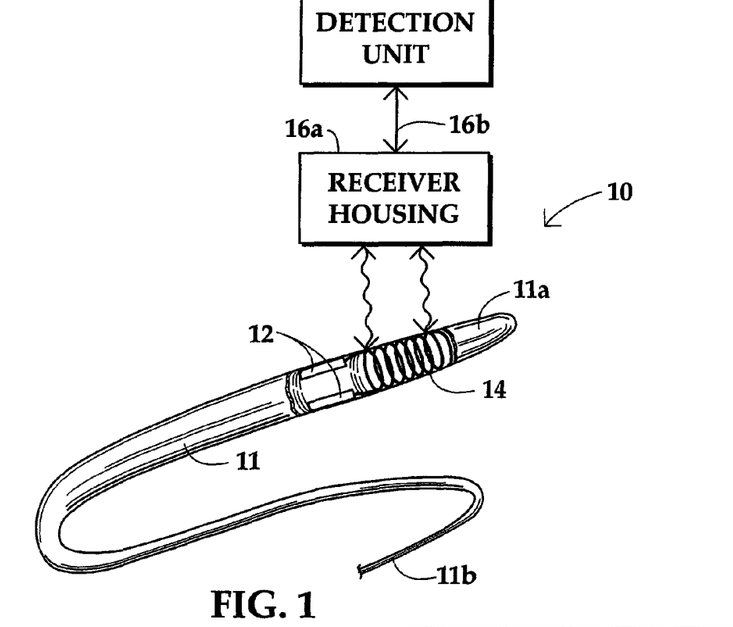
FIG. 1 is partially a schematic perspective view and partially a block diagram of a wireless pressure sensing system in accordance with the present invention.
Figure 5:
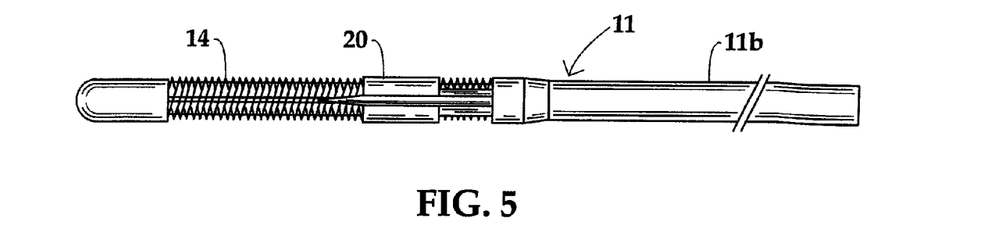
FIG. 5 is a schematic side elevational view of a distal end portion of a guide wire in accordance with the present invention, showing a coil implementing a floppy tip and utilized as the inductor of a pressure sensing resonance circuit and further showing the position of a variable-capacitance capacitor completing the resonance circuit, in accordance with the present invention.

As illustrated in FIG. 1, a pressure sensing guide wire system 10 comprises a guide wire 11 having a sensor 12 and coil 14 at its distal end portion 11a. FIG. 5 shows the mechanical arrangement of a floppy tip coil 14 and a capacitive sensor 20 forming a pressure sensing resonance circuit. The guide wire 11 may be inserted into the cardiovascular system of a patient. Small flexible devices, called catheters, may be guided over the guide wire 11 inserted through blood vessels and vascular structures of the patient, such as to the site of a damaged or diseased blood vessel, as typically performed in interventional cardiology. A detection unit 16 has a receiver housing 16a disposable external of the patient's body in the vicinity of the resonance circuit consisting of sensor 12 and coil 14. In a typical embodiment, receiver housing 16a carries an inductor 25 (FIG. 3) that may take the form of a flat coil, particularly a printed coil, attachable to the patient's back roughly at the location of the heart in case of coronary artery interventions. Such printed circuit coils are preferably disposable. The receiver housing 16a may be in contact with the patient's skin surface or introduced within the patient. Information from the sensor 12 is wirelessly detected by the receiver (detection resonance circuit 24, see FIG. 3) through the human body (soft or hard tissue). The body 11b of the guide wire 11, which is integrated with the sensor 12 and the coil 14, may be a typical guide wire used in interventional cardiology or interventional radiology (i.e., composed of non-corrosive biocompatible material(s)) and of a diameter and sufficiently flexibly and bendable to pass through blood vessel(s) or vascular structure(s) to a surgical or diagnostic target site in the patient (see also FIG. 5). The sensor 12 and detection unit 16 provide wireless detection of a physical variable, in particular blood pressure at such site, thus eliminating the need for a mechanical connection between the sensor and external detection equipment of the prior art.

Figure 2:
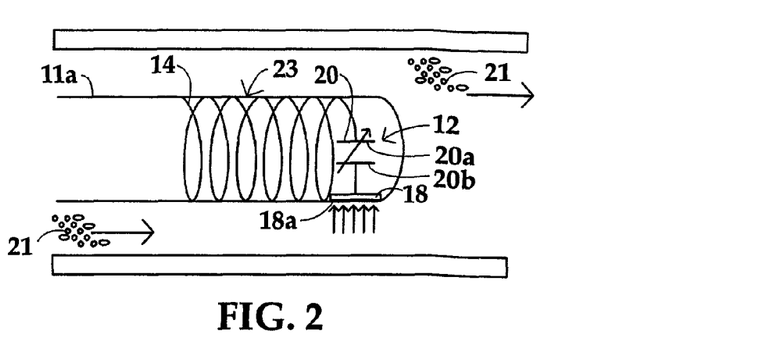
FIG. 2 is partially a schematic cross-sectional view and partially a circuit diagram of a distal portion of a guide wire in an artery of a patient, in accordance with the present invention.

FIG. 2 shows the distal portion 11a of the guide wire 11 in more detail. The distal portion 11a is a cone integrated to the body 11b at the distal end of the guide wire. The sensor 12 comprises a pressure sensitive element 18 mounted in the guide wire to detect the blood pressure surrounding the wire 11, and further comprises a variable capacitor 20, which is referred to herein as a pressure sensitive capacitive element. Pressure sensitive element 18 is connected to or part of a variable capacitor 20 whose capacitance value varies with amount of pressure upon element 18 from the blood about the distal portion 11a. The pressure sensitive element 18 has an outer surface 18a exposed to blood 21 about the distal wire portion 11a, and may be biased, such as by a spring, away from capacitor 20. Increased or decreased pressure upon the outer surface 18a moves the pressure sensitive element towards or away, respectively, from the capacitor, the change in distance resulting in a changing in the capacitive value of capacitor 20 and hence the resonance frequency of the resonance circuit 23 (FIG. 2) consisting of capacitor 20 connected to coil 14. More specifically, capacitor 20 may include a first plate element 20a and a second plate element 20b, where the latter is movably mounted relative to plate element 20a and guide wire 11 and coupled or entrained to pressure sensitive element 18 so that motion of the pressure sensitive element causes a change in the distance between plate 20b and 20a. Other capacitive pressure sensors may also be used, such as described for example in Sensors and Actuators A: Physical Vol 73, Issues 1-2, 9 Mar. 1999, Pages 58-67.

The position of the coil 14 and sensor 12 in the distal portion 11a of the guide wire may either be as shown in FIG. 1, in which the coil is more distal than the sensor 12, or vice versa, as shown in FIG. 2.

Figure 12A:
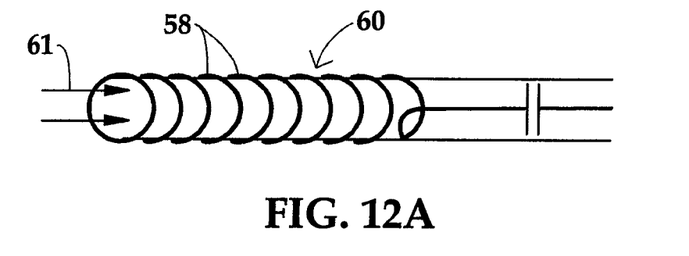
FIG. 12A is a diagram of another resonance circuit in the distal portion of a guide wire with a fixed value capacitor and a pressure sensitive inductor.
Figure 12B:
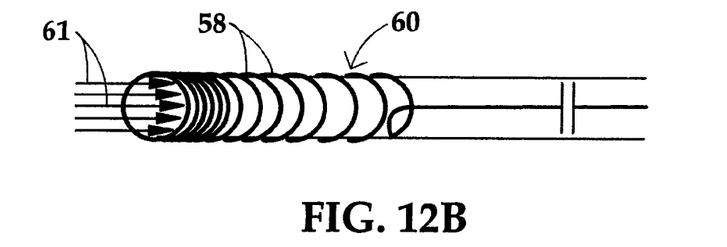
FIG. 12B is a diagram similar to FIG. 12A, showing the inductor with a shorter length owing to contraction in response to an increase in surrounding pressure.
Figure 13A:
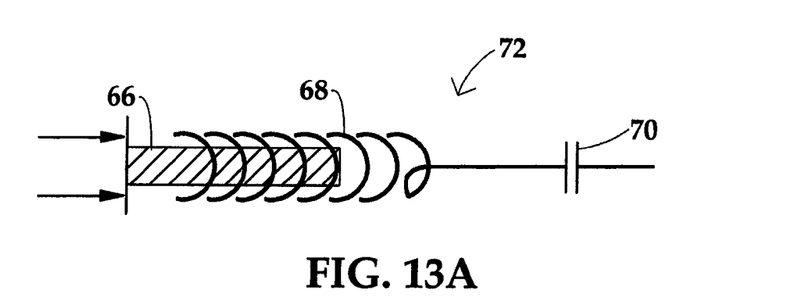
FIG. 13A is a diagram of yet another resonance circuit in the distal portion of a guide wire with a fixed value capacitor and a pressure sensitive inductor by virtue of a shiftable ferromagnetic inductor core.
Figure 13B:
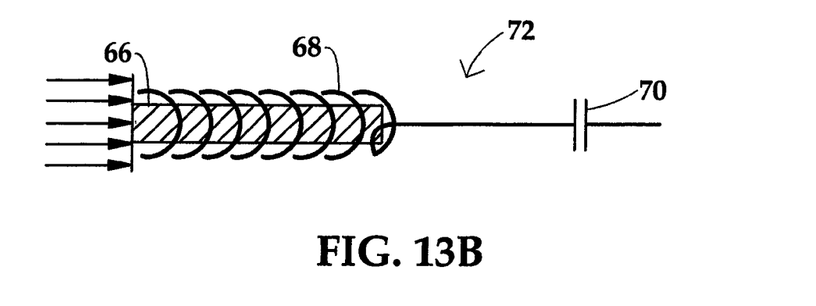
FIG. 13B is a diagram similar to FIG. 12A, showing the core inserted to a greater extent inside an inductor coil in response to an increase in surrounding pressure.

The coil 14 provides an inductance which may utilize the coil tip (or sections thereof) at the distal end of the guide wire, often referred to as the floppy tip. This inductor 14 and pressure sensitive capacitor 20 form a resonance circuit 23 with a resonance frequency varying with blood pressure fluctuations. In other embodiments, the capacitor can be of fixed value while the inductance of the coil changes according to the surrounding blood pressure. This can be accomplished by changing the length of a coil 56 or 60 according to surrounding blood pressure as shown in FIGS. 11A and 11B or FIGS. 12A and 12B. In the approach of FIGS. 12A and 12B, windings 58 of coil 60 are pressed in a longitudinal or axial direction of the guide wire in response to fluid pressure 61 exerted in that direction. Inductance changes can also be related to the surrounding blood pressure by changing the number of active windings of a coil or by changing the position of a ferromagnetic core 66 inside the coil as shown in FIGS. 13A and 13B.

Figure 3:
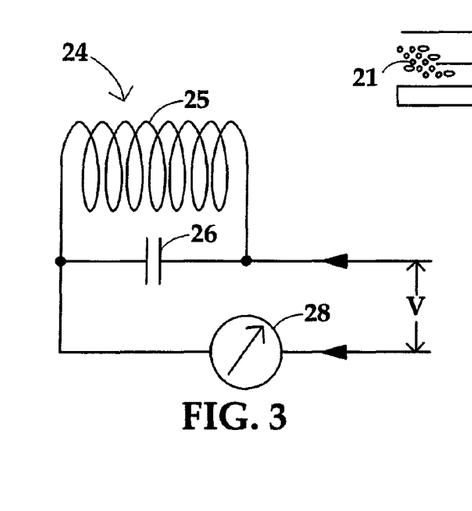
FIG. 3 is a circuit diagram of an external circuit of the wireless pressure sensing system of FIG. 1.

In the embodiment of the wireless pressure sensing guide wire system of FIGS. 1-3, an external or extracorporeal electro-magnetic field is created in response to an applied voltage by an external resonance (or detector) circuit 24 of the detection unit 16, comprising a capacitor 26 and an inductor (or coil) 25 as shown in FIG. 3. When both resonance circuits 23 and 24 are tuned to the same resonance frequency, a maximum energy transfer will take place from the external circuit 24 to the internal circuit 23, which is mounted inside the guide wire 11. Detuning of the circuit 23 through capacitance changes (caused by blood pressure variations) will vary the amount of transmitted energy to the external circuit 24. By recording the changes of transmitted energy, a blood pressure recording is provided, as via a current sensor 28. Thus, pressure values are detected without making an electrical connection by wire at the proximal guide-wire end or by switching the detector unit 16 into a receive-only mode relying on very weak signals being emitted from a free oscillation of the sensor circuit 12 after the power to the detector circuit 16 has been cut, as described in U.S. Pat. No. 6,517,481.

The detection circuit 24 may be disposed in housing 16a and electronically connected (e.g., via wires 16b) to the detection unit 16 which supplies power and varies the frequency of resonance circuit 24 in the operative frequency range of circuits 23 and 24, and a change in power/current monitor 28 detects the resonance frequency when circuits 23 and 24 are in resonance.

Figure 14:
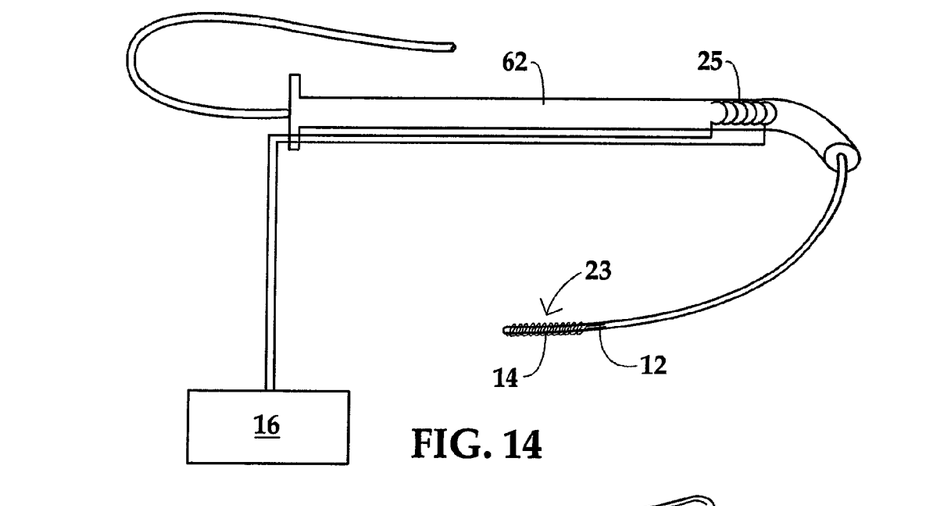
FIG. 14 is partially a schematic perspective view and partially a block diagram of another wireless or practically wireless pressure sensing system in accordance with the present invention, showing an external detection unit connected to an external coil located at a distal end of an insertion sheath.

Optionally, in order to improve the coupling between sensor circuit 23 and detector circuit 24, the coil 25 of detector circuit 24 may be located in an insertion sheath 62 rather than housing 16a as shown in FIG. 14. During use of the pressure sensing guide wire system of FIG. 14, the sheath 62 may be located inside the aorta of the patient and the distal sheath end at the aortic arch and all devices (guide wire 11, balloon catheters etc) are advanced through the sheath. This has the advantage of better coupling between sensor circuit 23 and detector circuit 24. The guide wire 11 typically contains a core wire which may be fabricated out of a ferromagnetic material to even further improve coupling, since sensor coil 14 and detector coil 25 surround the same ferromagnetic core as shown in FIG. 14.

Only one LC circuit 23 is provided in the guide wire 11: an inductance L consisting of wire windings or coil 14 in the floppy tip 11a of the wire 11 and a capacitor 20 which changes capacitance C with blood pressure.

The inductance L of a distal pressure-sensing coil or inductor may be varied by moving, in response to blood pressure, a ferromagnetic core member 66 inside a guide wire coil 68 which is connected together with a fixed-value capacitor 70 in a resonance circuit 72, as shown in FIGS. 13A and 13B. Alternatively, the resonance frequency of an LC circuit may be varied in accordance with blood pressure by changing the number of active windings of a variable-inductance coil. This change in the number of active windings may be accomplished by shifting a winding-contact element and the coil relative to one another. Pursuant to another approach, depicted in FIGS. 12A and 12B, the inductance is adjusted by compressing, through blood pressure, the coil 60 as shown in FIGS. 12A and 12B. Changing the length of the coil 60, in response to a blood pressure-induced axial force serves to vary the inductance of the coil. In another embodiment, shown in FIGS. 11A and 11B, a membrane 74 surrounding the coil 56 is compressed in a transverse or radial direction by the surrounding blood pressure 75. With windings 78 of coil 56 movably mounted relative to the guide wire and with the membrane 74 connected to the windings, the inward distortion of the membrane 74 causes the windings 78 to move laterally towards one another, in the longitudinal direction of the guide wire, thus modifying the active length of the coil 56 and varying the inductance proportional to blood pressure changes.

In system 10 of the present invention contact-less detection of a remote sensor is accomplished by detecting the resonant frequency of the sensor circuit 23 while the external detector circuit 24 is being powered up. The detection operation works as follows: the external high frequency oscillator sweeps across a frequency band. An electromagnetic field of different frequencies is generated while the power consumption of the external high-frequency oscillator is being monitored. The sensing LC circuit 23 absorbs a portion of the RF power of external high frequency oscillator mainly at its resonant frequency. The power, with which the external oscillator is supplied, will exhibit a change when the external circuit 24 and the sensing circuit 23 are in resonance. This change in power consumption of the external high frequency oscillator represents the resonance frequency of the LC sensor 12 which in turn is indicative of the blood pressure.

The detection unit 16 may have electronics for detecting when the power change occurs and displaying the corresponding blood pressure reading on a display. Such electronics may have a programmed controller or microprocessor (or other logic device), which calculates (or lookups up in a table in a memory) the corresponding blood pressure for the detected resonance frequency for output to the display. The relationship of resonance frequency to blood pressure may be in accordance with an equation, or calibrated with circuits 23 and 24 to provide a curve or look-up-table relating frequency to blood pressure stored in memory of the electronics for later use. See for example, see monitoring material properties in: Butler; Sensors and Actuators A 102 (2002) 61-66. The blood pressure monitoring process may be done periodically during interventional procedures or as needed to classify the hemodynamic significance of a lesion, so that the blood pressure about the site of intervention can be accurately measured.

Detection unit 16 is configured for detecting a change in blood pressure by detecting an absorption of less electromagnetic energy by resonance circuit 23 in response to the change in the inductance or capacitance of the pressure-sensitive LC circuit element. Detection unit may be programmed to calculate, or look up in a table, the pressure corresponding to the amount of reduction of energy absorption. Alternatively, detection unit 16 may induce detector circuit 24 to scan through a range of frequencies about the former resonance frequency, thereby picking up or detecting a new resonance frequency. Detection unit 16 may then report the new blood pressure associated with the newly detected resonance frequency.

Figure 4A:
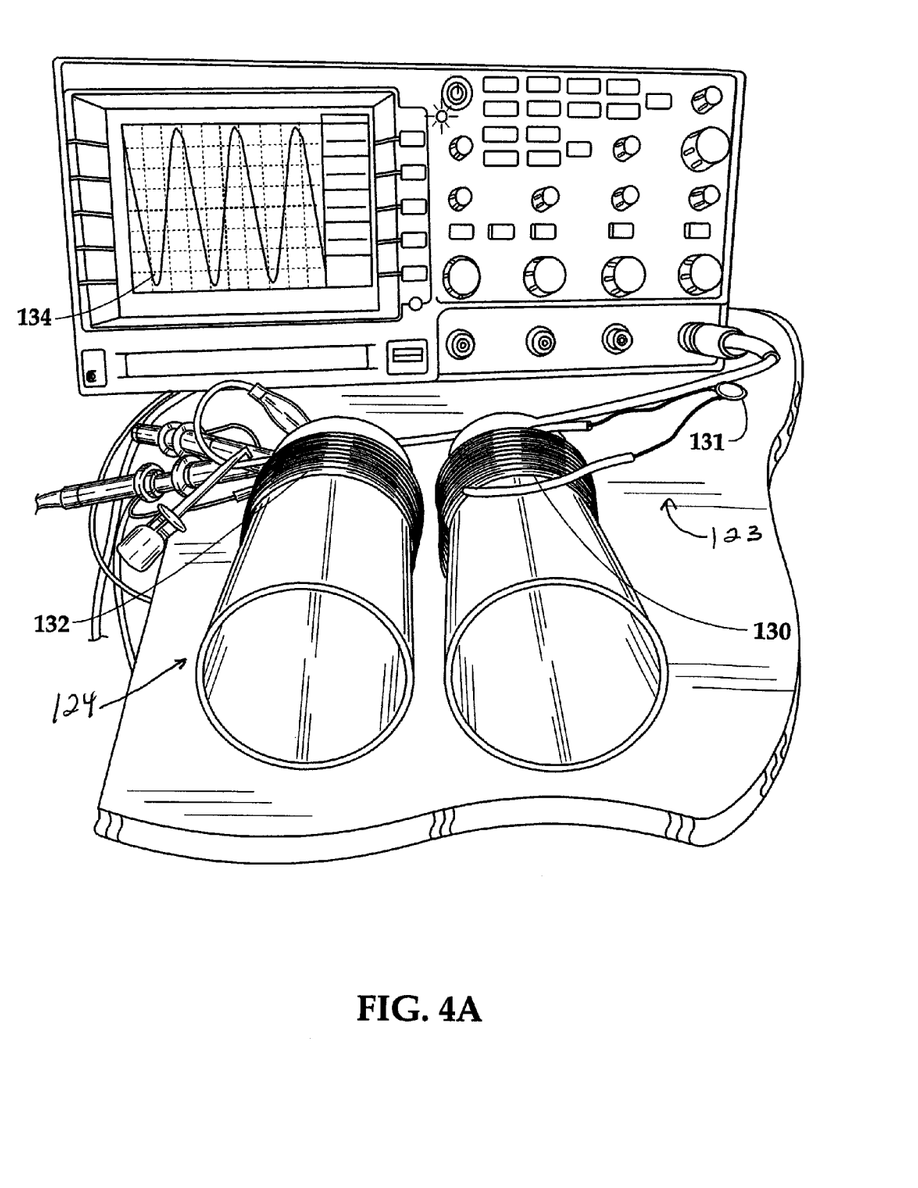
Figure 4B:
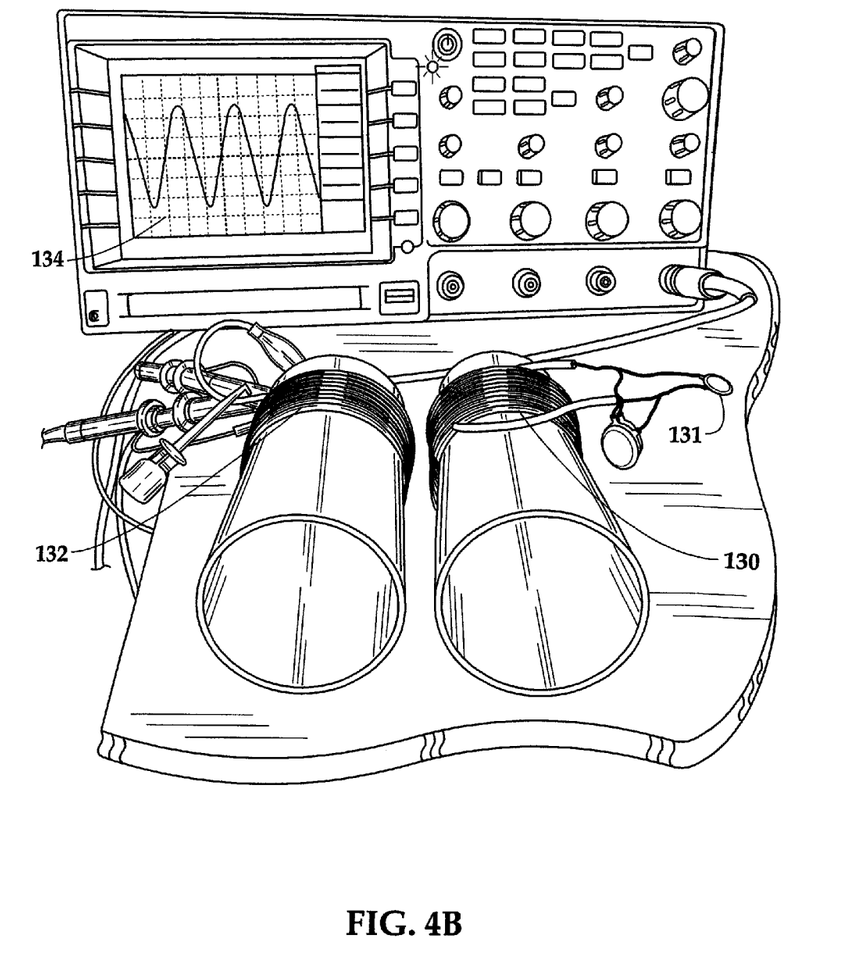

FIGS. 4A and 4B are two photographs illustrating resonance between two resonance circuits illustrating the operation of the present invention providing a sensor circuit 123, which corresponds to and functions the same way as sensor circuit 23, and a detector circuit 124, which corresponds to and functions the same way as sensor circuit 24 of system 10. The sensor circuit 123 for illustrative purposes is not shown in the desired form and configuration described earlier. The detector circuit 124 may also be in a different form than shown. In each figure, the right circuit illustrates the sensor circuit 123 having a coil 130 connected to capacitor 131, the left circuit illustrates the detector circuit 124 having a coil 132 connected to a capacitor (not shown), and the oscilloscope's leads are connected to the detector circuit. FIG. 4A shows the sensor circuit and the detector circuit in resonance and accordingly a high current on the oscilloscope' screen 134 at this frequency. A frequency oscillator (not shown) when such resonance circuits are in the desired form and configuration coupled to the detector circuit was varied until the high current was observed on the oscilloscope (i.e., from a change in power consumption of the detector circuit 24 when the two circuits illustrated are in resonance). To illustrate a pressure change (and hence capacitance), FIG. 4B illustrates the sensor circuit detuned with an additional capacitor 132 connected to capacitor 131, which reduces the current in the detector circuit and hence the observed current is now lower on the oscilloscope's screen 134. The frequency oscillating the detector circuit is now at the different frequency than the new resonance frequency of the sensor circuit due to the combined capacitance of capacitors 132 and 131 in the LC circuit 23 with coil 130.

From the foregoing description, it will be apparent that there have been provided a wireless pressure sensing guide wire and detector. Variations and modifications in the herein described apparatus, method, and system in accordance with the invention will undoubtedly suggest themselves to those skilled in the art.

Figure 6:
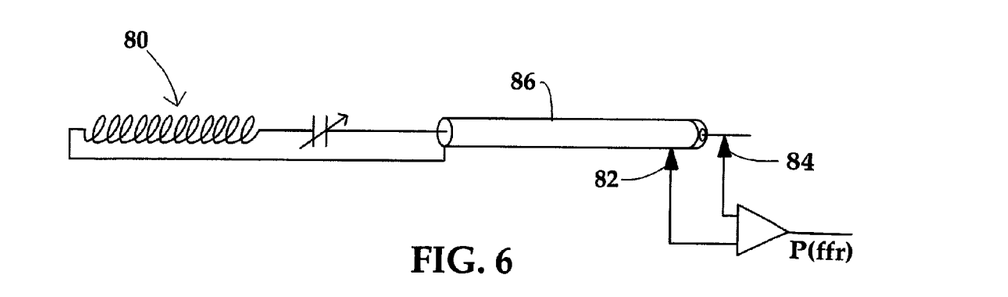
FIG. 6 is a circuit diagram showing a 2 contact version of pressure-sensing guide wire system in accordance with the present invention.

FIG. 6 is an electric circuit diagram showing the structure of the 2 contact pressure wire version. A resonance sensing circuit 80 at the distal wire end is identical to the one described above for the wireless version. Instead of wirelessly determining the change of the resonance frequency, two contacts 82 and 84 at the proximal wire end 86 are utilized.

Figure 7:
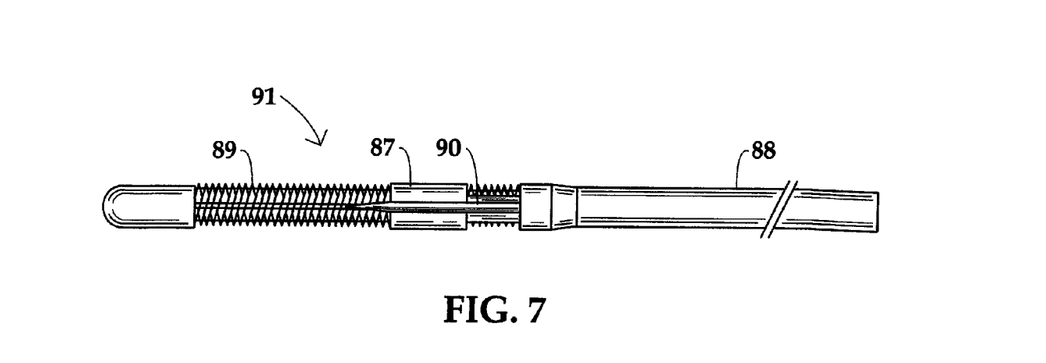
FIG. 7 is a schematic side elevational view of the 2 contact version of the pressure-sensing guide wire, demonstrating how a core wire and a hypotube are utilized as electrical conductors.
Figure 8:
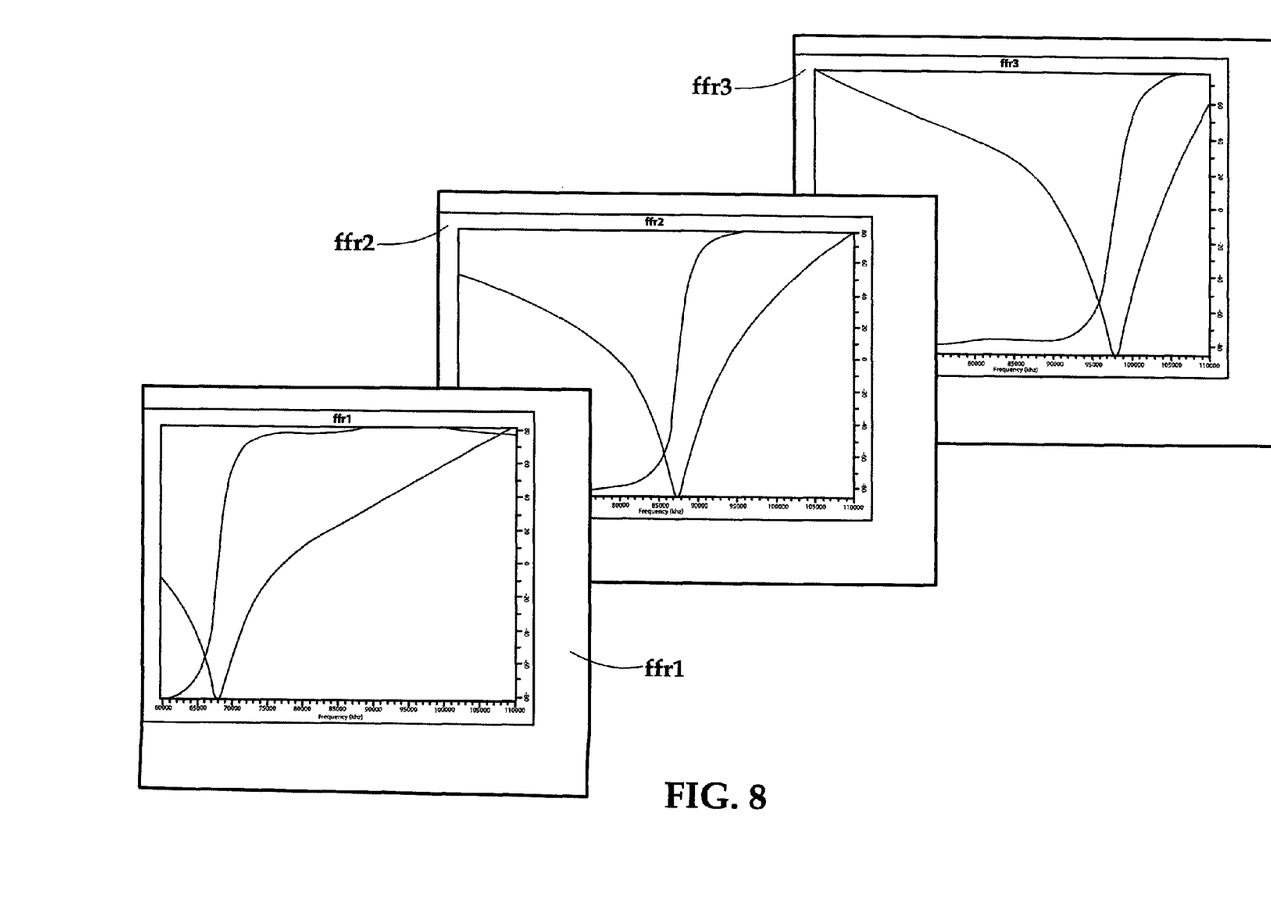
FIG. 8 is a series of three different resonance curves representing different capacitance values and concomitantly different pressure values.

FIG. 8 demonstrates the change in resonance frequencies for capacitive values of about 13 pF in screen ffr1, about 8 pF in screen ffr2 and about 7 pF in screen ffr3. A change of about 5 to 6 pF represents the physiological pressure range in this experiment and allows for unmistaken detection of the blood pressure values. FIG. 7 shows typical guide wire components utilized as electrical conductors to avoid having to integrate additional electrical wires into the guide wire structure, which negatively affects wire handling. The compromised wire handling of the commercially available pressure sensing guide wires represents a significant barrier towards widespread use of pressure sensing guide wires. As FIG. 7 demonstrates, the wire handling can be equal to non-pressure sensing guide wires by requiring only 2 electrical conductors in the form of the standard wire components of hypotube 88 and core wire 90). Core wire 90 is connected to a capacitor 87 and inductor or coil 89 of an LC pressure-sensing circuit 91.

Figure 9:
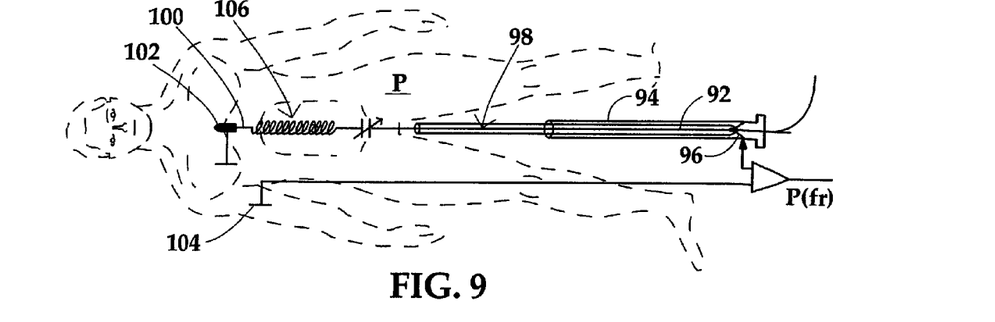
FIG. 9 is essentially a circuit diagram of a sheath contact version of a pressure sensing guide wire system in accordance with the present invention.
Figure 10:
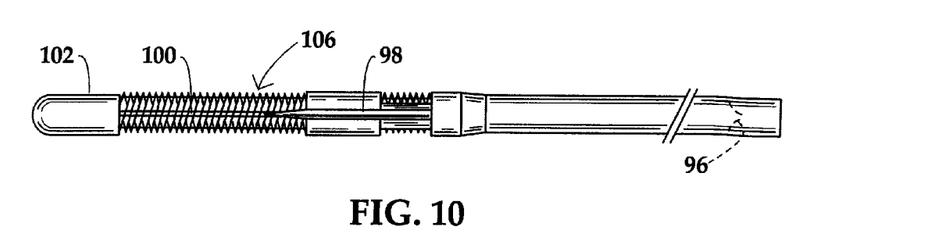
FIG. 10 is a schematic side elevational view of the sheath-contact pressure wire depicted as a circuit diagram in FIG. 9.
Figure 11A:
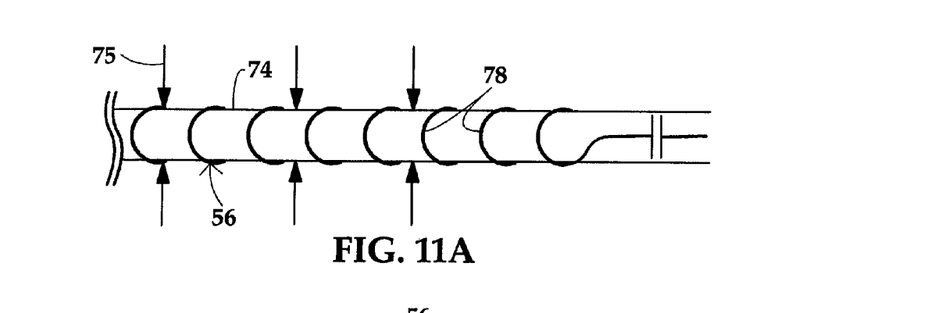
FIG. 11A is a diagram of a sensor resonance circuit in a distal portion of a guide wire, where the circuit includes a fixed value capacitor and a pressure sensitive inductor.
Figure 11B:
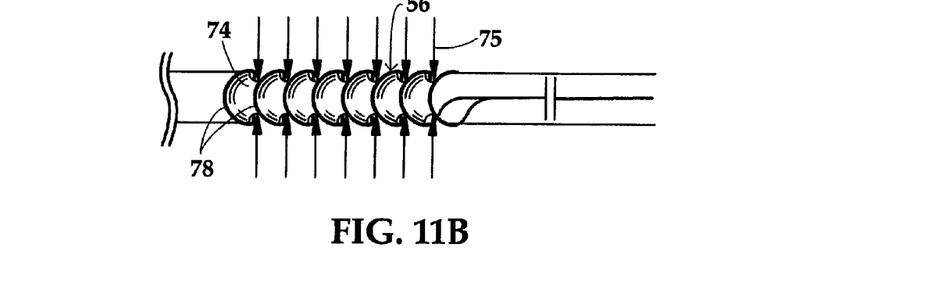
FIG. 11B is a diagram similar to FIG. 11A, showing the inductor with a shorter length owing to contraction in response to an increase in surrounding pressure.

FIG. 9 shows an alternative configuration which to the user appears wireless since a proximal guide wire end 92 does not need to be connected with a connector handle. Instead a sheath 94, which is part of any interventional procedure, contains a brush contact 96 to connect to the proximal end 92 of the guide wire 98, while a distal end 100 of the wire is in electrical contact via an electrode 102 with the patient P, who in turn is connected to ground potential through a ground electrode 104. This grounding technique is widely utilized in RF ablation procedures with a typical impedance of about 100 Ohms from RF electrode to ground. As can be seen in FIG. 8, the resonance frequencies, for the pressure wire configurations described here, are in the $10^{th}$ of MHz range (vs. KHz range for RF ablations), which reduces the serial impedance to ground to negligible values since the mostly capacitive impedance of the patient body is proportional to 1/f. An LC resonance circuit 106 at the distal wire end 100 is connected through electrode 102 at the distal tip of the wire 98 to the patient P who is connected to ground potential through the ground electrode 104. The other end of the resonance circuit 106 is connected to the wire body 98, either the hypotube and or core wire. The proximal end portion 92 of the wire 98 is not insulated in order to make contact with the contact brush 96 within the sheath as shown in FIG. 10. This has the same advantage as in the two contact version that wire handling is not compromised since standard wire components (hypotube and or core wire) are utilized as electrical conductor avoiding the insertion of additional electrical wires.

Figure 15:
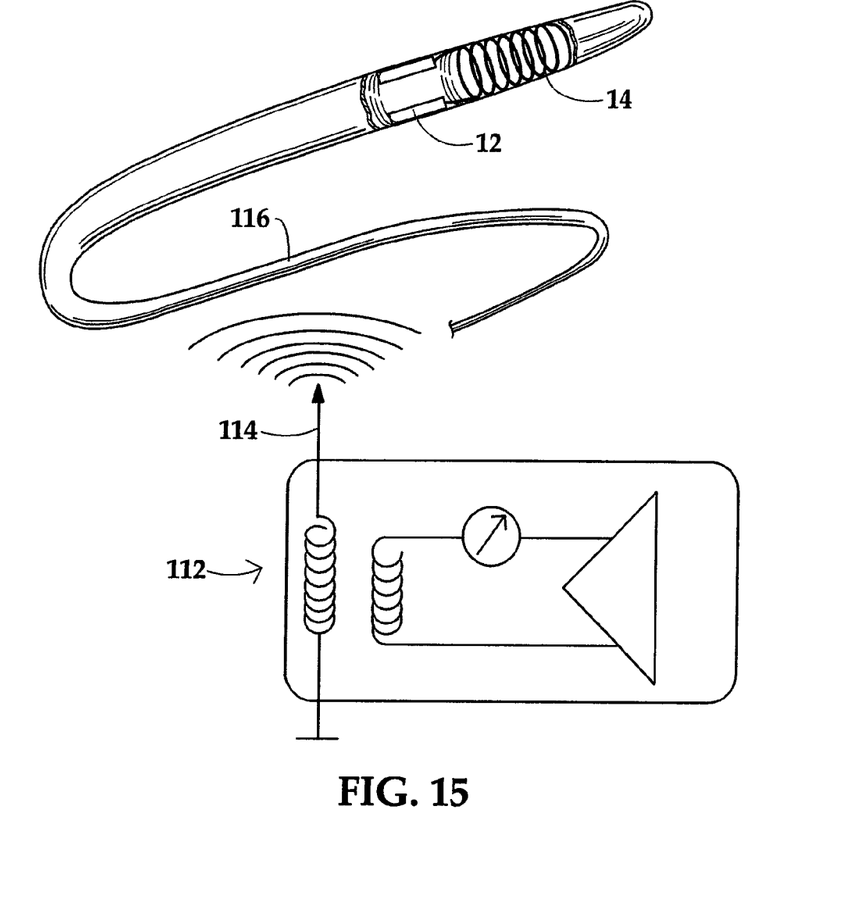
FIG. 15 is partially a schematic perspective view and partially a circuit diagram of another contactless pressure sensing system in accordance with the present invention, where an external detector includes a radio transmitter.
Figure 16:
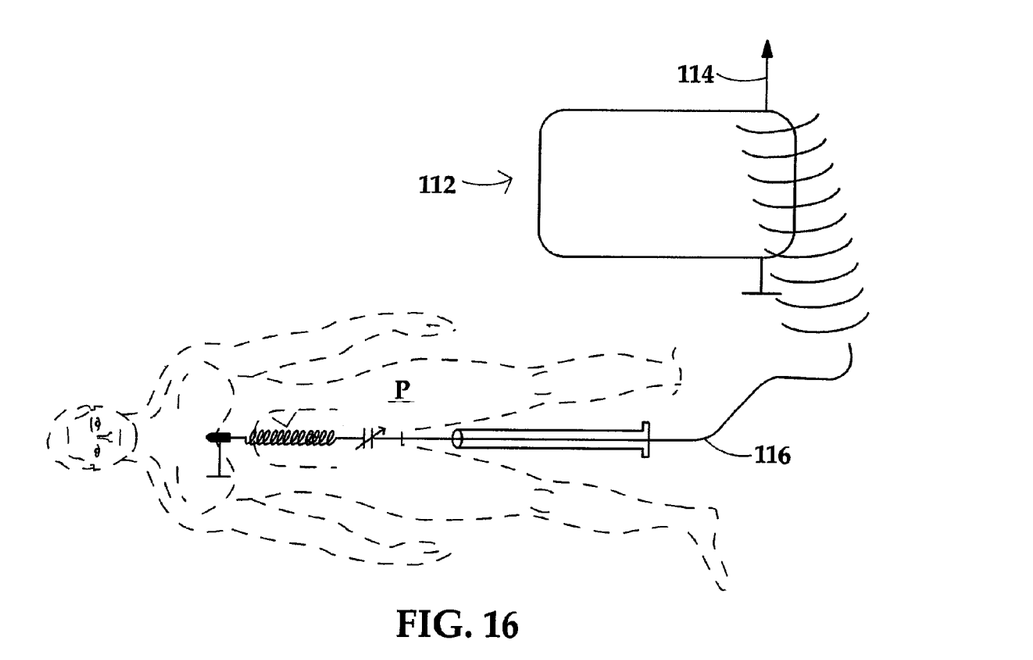
FIG. 16 is a schematic diagram of the contactless configuration of FIG. 15, showing how a proximal guide wire end acts as an opposite (receiver) antenna.

In another embodiment, a wireless coupling is accomplished with an external radio transmitter 112, as shown in FIG. 15. An antenna 114 of the external radio transmitter 112 interacts with the proximal guide wire end 116, which acts as a receiver antenna, as shown in FIG. 16. Except for the coupling through antennas this configuration functions as described for the wireless system 10 with the detector unit 16 and the guide wire 11 as shown in FIG. 1.

Figure 17:
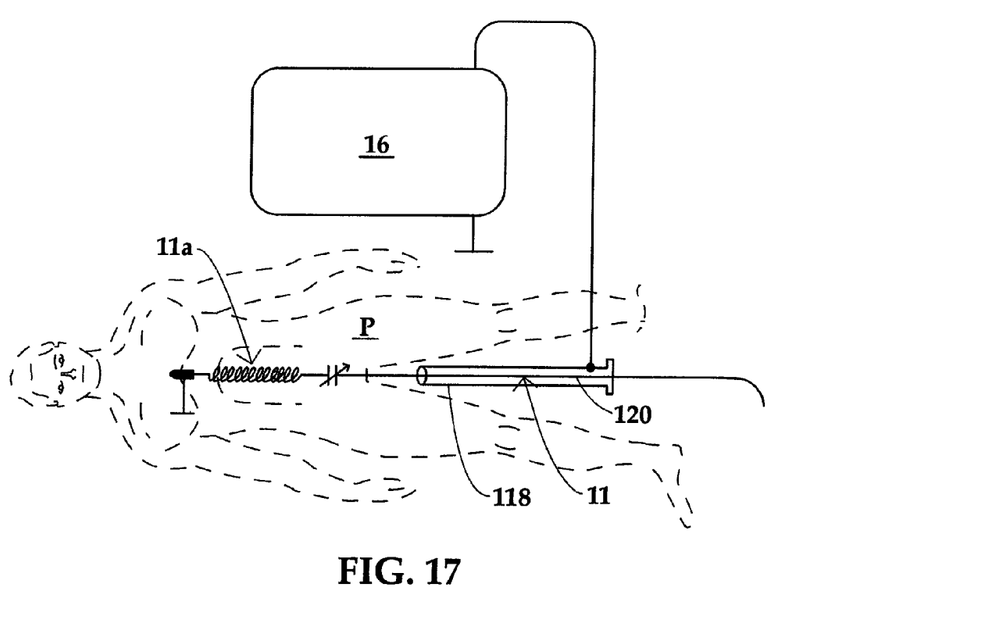
FIG. 17 is a schematic diagram of another contactless configuration wherein a detector and guide wire are coupled capacitively through an insertion sheath.

In yet another embodiment, the coupling between detector unit 16 and the resonance circuit 23 in the guide wire 11 is accomplished capacitively as shown in FIG. 17. An insertion sheath 118 might be equipped with a special metallic layer which acts as one capacitive electrode while the proximal guide wire section 120 inserted through the sheath acts as the opposite electrode. Instead of a special metal layer, the metallic braid many sheaths utilize for torqueabilty could be utilized.

Figure 18:
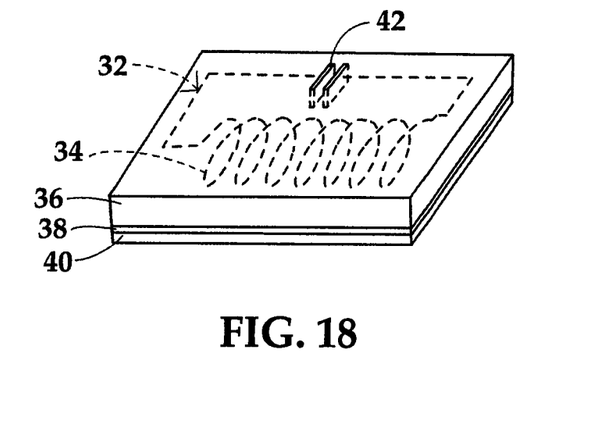
FIG. 18 is a schematic perspective view of an adhesive patch carrying a resonance circuit inductor in accordance with the present invention.

As depicted in FIG. 18, an external or detector resonance circuit 32 may include a printed disposable coil 34 attachable to a patient near an intervention site. Coil 34 may be embedded in a strip 36 of polymeric material that is provided with an adhesive layer 38 and a removable cover sheet 40. A capacitor 42 of the LC resonance circuit 32 may be provided in strip 36 or separately therefrom.

Figure 19:
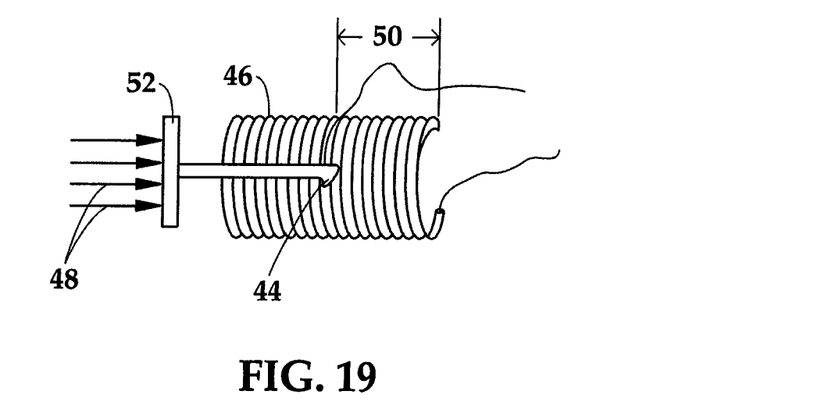
FIG. 19 is a schematic side elevational view of an inductor or coil having a number of active windings that varies in accordance with external fluid pressure.

As shown in FIG. 19, a resonance circuit on a guide wire may have a movable electrical contact 44 shiftable relative to a coil 46 so that changes in pressure 48 of an external fluid (e.g., blood) results in shifting of the contact relative to the coil and changing the active length 50 of the coil, thereby varying an inductance of coil and concomitantly the resonance frequency of the resonance circuit. The movable electrical contact 44 is coupled to a plate or disk 52 that moves relative to the guide wire in response to changes in external fluid pressure 48.

The invention claimed is:

1. A system for detection of blood pressure in a blood vessel comprising:
   a guide wire;
   a sensor circuit provided at least in part at a distal end of said guide wire, said sensor circuit including a capacitor and a coil disposed at said distal end of said guide wire, at least one of said coil and said capacitor being responsive to changes in pressure of fluid external to said guide wire;
   a detector operatively connected to said sensor circuit for monitoring said sensor circuit and determining the pressure of the external fluid; and
   an insertion sheath, said guide wire extending through said insertion sheath, said sensor circuit being operatively connected to said detector via a ground electrode at a distal end of said guide wire and via a brush contact inside said insertion sheath.

2. The system defined in claim 1 wherein said coil and said capacitor are coupled to each other to form a resonance circuit, at least one of said coil and said capacitor being responsive to changes in pressure of fluid external to said guide wire such that said resonance circuit has a resonance frequency that varies in accordance with changes in pressure of the external fluid.

3. The system defined in claim 2 wherein said coil is configured to have an inductance that is variable depending on changes in pressure of fluid external to said guide wire.

4. The system defined in claim 3 wherein said coil is provided with a ferromagnetic core that is movably mounted to said guide wire and partially disposed inside said coil so that changes in pressure of said external fluid results in a shifting of said core relative to said coil, thereby varying an inductance of said coil and concomitantly the resonance frequency of said resonance circuit.

5. The system defined in claim 3 wherein said resonance circuit has a movable contact shiftable relative to said coil so that changes in pressure of said external fluid results in shifting of said contact relative to said coil and changing of an active length of said coil, thereby varying an inductance of said coil and concomitantly the resonance frequency of said resonance circuit.

6. The system defined in claim 3 wherein said coil has windings that are shiftably mounted to said guide wire so that changes in pressure of said external fluid results in a change in an effective length of said coil, thereby varying an inductance of said coil and concomitantly the resonance frequency of said resonance circuit.

7. The system defined in claim 2, wherein said detector is operatively connected to said resonance circuit for monitoring said resonance frequency and determining the pressure of said external fluid.

8. The system defined in claim 7 wherein said resonance circuit is a first resonance circuit, said detector including a second resonance circuit disposable outside of a patient, said second resonance circuit being electromagnetically couplable to said first resonance circuit for determining said resonance frequency by detecting when said first and said second resonance circuits are in resonance.

9. The system defined in claim 8 wherein said detector is configured to monitor power consumption of the second resonance circuit.

10. The system defined in claim 8 wherein said second resonance circuit includes a printed disposable coil attachable to a patient near an intervention site.

11. The system defined in claim 8 wherein said second resonance circuit is mounted on said sheath, said guide wire extending through said sheath.

12. The system defined in claim 1 wherein said capacitor is configured to have a capacitance that varies in response to changes in an external pressure.

13. The system defined in claim 12 wherein said capacitor includes a first plate element and a second plate element, at least said second plate element being movably mounted to said guide wire so that changes in pressure of said external fluid results in a shifting of said second plate element and a change in a distance or separation between said first plate element and said second plate element, thereby varying said capacitance and concomitantly the resonance frequency of said resonance circuit.

14. The system defined in claim 1 wherein said detector includes a radio transmitter/receiver operatively connectable to said sensor circuit via a proximal wire end acting as a receive/transmit antenna.

15. A system for detection of blood pressure in a blood vessel comprising:
   a guide wire;
   a sensor circuit provided at least in part at a distal end of said guide wire, said sensor circuit including a capacitor and a coil disposed at said distal end of said guide wire, at least one of said coil and said capacitor being responsive to changes in pressure of fluid external to said guide wire; and a detector operatively connected to said sensor circuit for monitoring said sensor circuit and determining the pressure of the external fluid, wherein said guide wire has a core member and a hypotube, said detector being connected to said sensor circuit via two electrical contacts located at a proximal end of said guide wire, one of said electrical contacts being connected to said core member and another of said electrical contacts being connected to said hypotube.

16. A system for detection of blood pressure in a blood vessel comprising:

a guide wire;

a sensor circuit provided at least in part at a distal end of said guide wire, said sensor circuit including a capacitor and a coil disposed at said distal end of said guide wire, at least one of said coil and said capacitor being responsive to changes in pressure of fluid external to said guide wire;

a detector operatively connected to said sensor circuit for monitoring said sensor circuit and determining the pressure of the external fluid; and an insertion sheath, said guide wire extending through said insertion sheath, a metal layer or a braid being disposed inside the sheath, said metal layer or braid coacting together with said guide wire to form a capacitor that couples said detector to said sensor circuit.

* * * * *